United States Patent [19]

Schael

[11] 4,231,366
[45] Nov. 4, 1980

[54] BLOOD FLOW MONITORING AND CONTROL APPARATUS

[75] Inventor: Wilfried Schael, Bad-Homburg-Dornholzhausen, Fed. Rep. of Germany

[73] Assignee: Dr. Eduard Fresenius Chemisch-Pharmazeutische Industrie KG Apparatebau KG, Bad Homburg von dur Hahe, Fed. Rep. of Germany

[21] Appl. No.: 822,928

[22] Filed: Aug. 8, 1977

[30] Foreign Application Priority Data

Aug. 12, 1976 [DE] Fed. Rep. of Germany ....... 2636290

[51] Int. Cl.³ .............................................. A61M 1/03
[52] U.S. Cl. ........................ 128/214 E; 128/DIG. 13
[58] Field of Search ................... 128/2 F, 2 G, 214 E, 128/214 R, DIG. 3, DIG. 5, DIG. 7, DIG. 12-13; 23/258.5 R; 210/321 B, 321 A; 422/44, 48

[56] References Cited

U.S. PATENT DOCUMENTS

| 2,625,933 | 1/1953 | Salisbury | 128/DIG. 3 |
|---|---|---|---|
| 3,609,379 | 9/1971 | Hildebrandt et al. | 128/DIG. 13 X |
| 3,659,603 | 5/1972 | Oses | 128/214.2 |
| 3,701,345 | 9/1970 | Heilman et al. | 128/2 R X |
| 3,756,234 | 9/1973 | Kopp | 210/321 B X |
| 3,802,432 | 4/1974 | Djerassi | 23/258.5 R X |
| 3,830,234 | 8/1974 | Kopp | 128/214 R |
| 3,838,682 | 10/1974 | Clark et al. | 128/2 G |
| 3,882,861 | 5/1975 | Kettering et al. | 128/DIG. 12 X |
| 3,890,969 | 6/1975 | Fischel | 128/DIG. 3 |
| 3,896,803 | 7/1975 | Mason | 128/214 R |
| 3,908,653 | 9/1975 | Kettering | 128/214 R |
| 3,946,731 | 3/1976 | Lichtenstein | 23/258.5 R X |

FOREIGN PATENT DOCUMENTS 2220281 10/1974 France .................................. 128/214 E

OTHER PUBLICATIONS

Twiss, E. E., "One-Cannula Haemodialysis," Lancet, Nov. 21, 1964, p. 1106.

Primary Examiner—Robert W. Michell
Assistant Examiner—Francis J. Jaworski
Attorney, Agent, or Firm—W. G. Fasse; W. W. Roberts

[57] ABSTRACT

The present blood flow monitoring and control apparatus is especially useful in connection with the so-called single needle technique, for example, for treatments such as dialysis, perfusion, or diafiltration. The blood pressure control is accomplished by a measuring chamber including a pressure equalizing device operatively connected between the blood cleaning apparatus and the blood pump. Sensors are operatively connected to the volume measuring chamber. The volume sensors provide electric control input signals to a control circuit which in turn controls the blood pumps and/or valves. A reading may be provided on a display or an alarm may be given when the blood pressure or blood quantity or volume is not within predetermined limits as calculated by an electronic computer.

12 Claims, 9 Drawing Figures

BLOOD FLOW MONITORING AND CONTROL APPARATUS

BACKGROUND OF THE INVENTION

The present invention relates to a blood flow monitoring and control apparatus which is especially useful in connection with such treatments as blood dialysis, blood perfusion and blood diafiltration by utilizing only one connection point in the patient's blood circulatory system which is also referred to as the single needle technique.

The various methods for the detoxification of the blood require an external blood circulating system outside the human body. In other words, it is necessary to extract the blood with suitable means from the patient's inner blood circulatory system and to conduct the blood through the detoxification apparatus whereupon it must be returned back into the patient's internal blood circulatory system. Accordingly, normally two connecting points are necessary in the patient's blood circulatory system in order to maintain a continuous blood flow. Such connecting points are normally established by inserting a cannula through the skin and into a blood vessel of the patient.

The penetration of the skin by the cannula is painful to the patient and since the cannulas have a substantial diameter, damage to the skin at the point of penetration cannot be avoided. In many instances it has become a serious problem to find repeatedly new points for penetration by the cannula, especially where a patient must undergo repeated treatments at short intervals. These problems resulted in the development of the so called single needle technique for the performance of which only a single penetration cannula is required.

The single penetration point is sufficient because under the single needle technique blood is withdrawn from the inner circular system and returned into such inner system in an alternating manner whereby a phase of withdrawal is followed by a phase of return and so forth. This operation is discontinuous and, as a result, the efficiency of the treatment is somewhat reduced. However, such reduction in the treatment efficiency may easily be compensated by extending the duration of the treatment.

Conventional devices mostly control the alternating withdrawal and return of blood, either by predetermining the duration of the continuous change between withdrawal and return, or by making such continuous change dependent on the pressure conditions prevailing in the external blood circulatory system. The first mentioned method, which employs a predetermined timing, is technically very simple. However, it has the disadvantage that the pressure conditions in the external blood circulatory system are subject to undefined changes or variations.

The pure timing control does not constitute an optimal solution according to present day opinions of the experts, because the blood pressure is of substantial importance for the efficiency of a blood cleaning treatment, since the blood pressure in the blood cleaning apparatus influences the passage of the liquid through the dialyzer or through the filter membrane. Such a disadvantage is avoided in a system controlled in response to pressure provided that the control is arranged in such a manner that the pressure changes continuously back and forth between a fixed lower limit value and a fixed upper limit value, thereby defining a predetermined mean blood pressure value.

For several reasons it is possible in the pressure controlled system to establish merely a positive mean blood pressure value. Incidentally, this also applies to the time controlled system. This is so, because for safety purposes, the lower pressure limit may at best be a zero pressure value, because of the danger that contaminated liquid could possibly be sucked back into the internal circulatory system of the patient through a possibly defective dialyzer or filter membrane and due to the further danger that air might be sucked into the system due to leaks in the conduits of the external circulatory system. On the other hand, the upper pressure limit must be above the lower pressure limit by a certain minimal value in order to obtain a sufficient volume movement for each operational cycle. Thus, in such systems, only a positive mean blood pressure may be established. In certain instances, for example in the dialysis treatment of children, this requirement of the prior art systems may cause problems, because the liquid withdrawn from the circulatory system of a child must necessarily be very small.

Another danger occurs in both systems due to the continuous alternating loading of the dialysis or filter membrane, whereby the risk of a leak in the dialysis membrane is increased relative to a system in which the pressure load on the membrane is constant.

Yet a further disadvantage in the pressure controlled system alternating between blood withdrawal and blood return is seen in that the respective transported blood volume is not defined from the very start. Rather, the transported blood volume depends on the ability of the system to yield to the prevailing pressure. Such pressure yielding depends, for example, on the blood filling in the conventional air removal chamber. Depending on the manner of operating the system or on the quantity of air collected in such a chamber, the blood filling level in the air separation chamber may vary substantially. Furthermore, a volume shift or transport which is too small as well as a volume shift or transport which is too large in each cycle is also disadvantageous for medical reasons. In the first instance in which the volume shift is too small, the efficiency of the treatment is diminished. In the second instance in which the shifted volume of blood is too large, the volume variations in the internal blood circulatory system of the patient may also be too large.

It should also be mentioned here, that a break in the membrane or a larger leak in the conduit system acts as an infinite pressure yieldability. Stated differently, any switch-over is not accomplished and large quantities of blood may be lost through the leak unless additional safety measures are employed. However, such additional safety measures constitute a further increase of the apparatus expenses which in the pressure responsive control system is very large to begin with.

Due to the just mentioned disadvantages of prior art systems, the so called single needle technique has not been used on a large scale heretofore in spite of the advantages which this type of method does not provide in principle. Especially in the dialysis treatment in the patient's home, the single needle technique has hardly been used heretofore, mainly because the presently available systems are too uncertain in their function and also rather involved and hence it is difficult to operate these systems.

OBJECTS OF THE INVENTION

In view of the foregoing it is the aim of the invention to achieve the following objects, singly or in combination:

to provide an apparatus for the above mentioned purposes which is simple in its structure and easily understandable in its function and which further avoids the above mentioned disadvantages of the prior art systems;

to control the volume of blood withdrawal and volume of blood return in such a manner that an exceeding or a falling below of the filling level in a measuring chamber is automatically corrected by electronic circuit means which also may provide an indication and/or alarm;

to influence the blood flow in such a manner that during the blood withdrawal phase the blood flow rate is higher in the artery leg than in the vein leg of the branching junction member and that the flow rate is reversed during the return phase;

to ascertain the mean blood flow value;

to provide an alarm signal in response to the fact that the mean blood flow value exceeds or falls below a pre-selected value;

to ascertain and display the total quantity of blood subjected to the treatment;

to precisely define the ratio between the two partial flows, whereby a partial flow may be passed for the second time through a treatment device, whereby to increase the treatment efficiency; and to minimize the pain which the treatment may cause to the patient, especially as compared to methods employing two penetration points into the internal blood circulatory system of a patient.

SUMMARY OF THE INVENTION

According to the invention there is provided a blood flow monitoring and control apparatus suitable for treatment such as dialysis, perfusion, and diafiltration employing the single needle techniques which is characterized in that between the blood cleaning device and the blood pump in the vein portion of the system there is arranged a measuring chamber, preferably with a blood pressure equalization device, wherein sensor means are arranged to sense and monitor the blood in the measuring chamber to provide signals to a control mechanism which in turn controls the blood supply and withdrawal from the measuring chamber. Preferably, the sensors are supported in a holding mechanism in which they may be adjustable in their position.

According to a further feature of the invention the normal changes or variations in the filling level of the measuring chamber are limited by tube level sensors, whereas two further level sensors are provided for indicating the falling below or the exceeding of the normal filling level. The signals of these sensors are applied to an electronic circuit arrangement which controls the blood pumps for withdrawing blood from and/or returning blood into the patient, either by stopping or by starting these pumps. These signals from the sensors may also be used to provide alarm signals to indicate or display any nonpermissible operational condition.

The electronic control circuit according to the invention is arranged in such a manner that the blood pumps and/or the conduit valves are controlled so as to maintain a higher blool volume flow rate in the artery leg of a branching junction member during the blood withdrawal phase of the treatment while the volume flow rate in the vein leg of said member is lower during said withdrawal phase. During the blood return phase the flow rates are respectively opposite in said artery leg and vein leg of said branching junction member.

Preferably, an electronic computer is arranged for cooperation with the electronic control circuit in order to calculate the mean blood flow value for each operational cycle. Further, an indicating device may be connected to the computer for displaying such mean value.

According to the invention a monitoring circuit arrangement may be combined with the electronic control circuit or with the computer which will ascertain the fact that the actual measured value falls below a preselected mean blood flow value or that the blood flow has been interrupted altogether. The monitoring circuit may also provide an alarm signal in response to the automatic recognition of the just mentioned operational conditions. A further indicating device such as a counter or the like may be connected to the computer in order to indicate the total blood quantity employed in the particular treatment.

BRIEF FIGURE DESCRIPTION

In order that the invention may be clearly understood, it will now be described, by way of example, with reference to the accompanying drawings, wherein.

DETAILED DESCRIPTION OF PREFERRED EXAMPLE EMBODIMENTS

Figure 1:
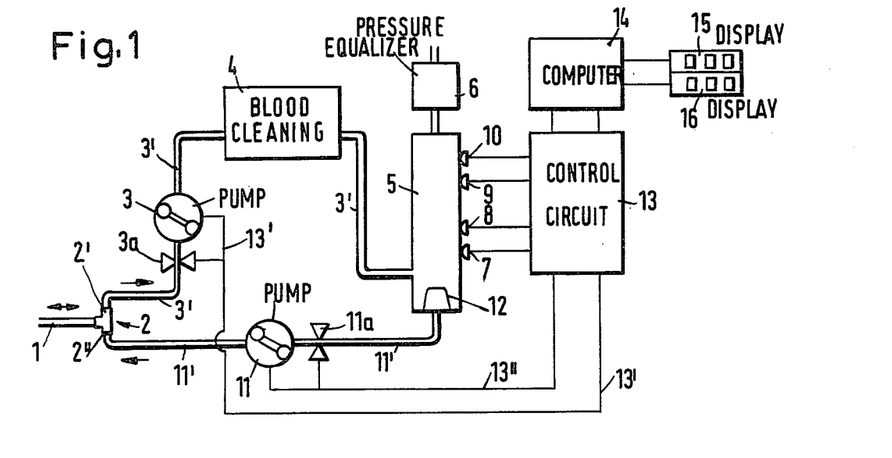
FIG. 1 illustrates a schematic diagram of the blood flow circuit as well as the control and computer circuit.

Referring to FIG. 1, the needle or cannula 1 to be inserted into the patient's internal blood circulatory system is connected to a branching junction member 2. One leg 2' of the junction member 2 is connected to the artery conduit 3' leading through a valve 3a into the artery pump 3. The output port of the pump 3 is connected through a further section of the artery conduit 3' to a blood cleaning device 4. A further section of the artery conduit 3' connects the output of the blood cleaning device 4 laterally into a measuring chamber 5. The second leg 2" of the junction member 2 is connected through the further conduit means 11' constituting vein conduit means, to a vein pump 11 which in turn is connected through valve means 11a to the output port of the measuring chamber 5. Screening or sieve means 12 separate the outlet port of the chamber 5 from the internal volume of said chamber 5. The valves 3a and 11a may, for example, be of the well known type capable of clamping a flexible conduit to thereby close it, for example, in response to an electrical signal which operates an electromagnet to actuate the clamping device.

The measuring chamber 5 has a further port connected to a pressure equalizing device 6 to be described in more detail below with reference to FIG. 5. Further, the chamber 5 is arranged to cooperate with, for example, four sensors 7, 8, 9, and 10. These sensors will be described in more detail with reference to FIGS. 3 and 4. The sensors 7, 8, 9, and 10 produce electrical signals supplied to a control circuit 13 which in turn is operatively connected to a computer circuit 14. The output of the computer circuit 14 may also be connected to display devices 15 and 16. Further, the control circuit 13 is connected through an electrical control connection 13' to the pump 3 and to the valve 3a. Similarly, a further electrical control line 13" connects to the pump 11 and to the valve 11a. For example, the display or indicator device 15 may provide an indication of the mean value of the blood flow and the indicating or display device 16 may provide an indication of the total blood volume involved in any particular treatment procedure.

Figures 2, 3:
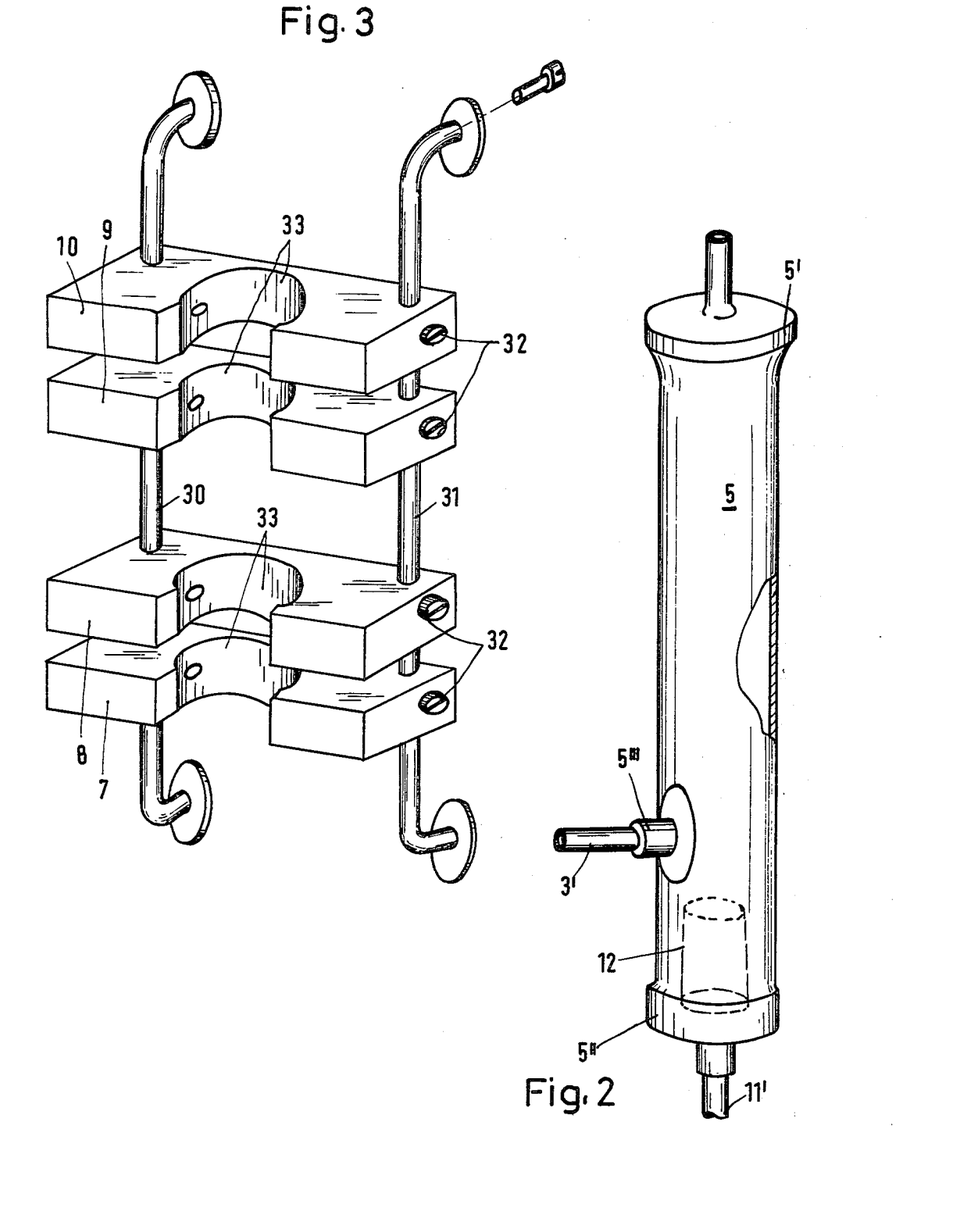
FIG. 2 illustrates the measuring chamber in more detail.
FIG. 3 illustrates the position adjustable arrangement of the blood sensors, whereby the measuring chamber is omitted for clarity.

FIG. 2 illustrates the measuring chamber 5 in somewhat more detail. This chamber 5 corresponds substantially to a conventional venous drip chamber which is part of a blood conduit or hose system manufactured for single or one time use purposes, to be thrown away thereafter to avoid the cleaning and sterilizing procedure. The chamber 5 may, for example, have a diameter of 25 mm and a length of 120 mm. An upper cup 5' connects the chamber 5 through a piece of hose to the pressure equalizer 6. The lower cup 5" connects to the vein conduit hose 11' and the sieve or screen means 12 form part of the cup 5" to prevent blood clots from returning into the internal blood circular system of the patient. According to the invention, the input port 5'" is laterally connected to the chamber 5 and leads to the blood cleaning device 4 through a section of the artery conduit 3'. The cups and the port are connected to the chamber 5 proper by conventional means, for example, by adhesives or by plastic welding.

FIG. 3 shows an example of how the sensors 7, 8, 9, and 10 may be arranged for cooperation with the transparent walls of the measuring chamber 5. Two holding rods 30 and 31 may be conventionally connected to the front or control panel of the entire system. Each sensor 7, 8, 9, and 10 is so arranged that its position may be vertically adjusted up and down along the holding rods 30 and 31 and the sensors may be fixed in position by set screws 32. Each sensor is provided with a substantially semi-circular recess 33 so dimensioned relative to the outer diameter of the tubular chamber 5, that the latter may be held in a secure position in these recesses 33.

Figure 4:
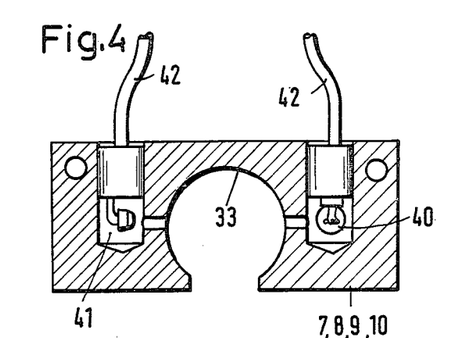
FIG. 4 illustrates a horizontal section through one example embodiment of a sensor.

FIG. 4 illustrates a sectional view through a sensor 7, 8, 9, or 10. All sensors have the same structure including a light source 40 and a photo-transistor 41 connected to the control circuit through electrical conductors 42. Since the blood is sufficiently opaque, it blocks the passage of light from the light source 40 to the photo-transistor 41 when it reaches the level corresponding to the adjusted position of the respective sensor. The resulting signal is evaluated in the control circuit 13 and employed for the control of the pumps and valves, as will be described in more detail below. The signals are also employed for the computation of a mean blood flow value and of a value indicating the total blood volume passing through the measuring chamber 5 in a certain period of time. Such measurements are possible because the volume of the chamber 5 is known and so are the adjusted positions of the sensors 7, 8, 9, and 10 as well as their exact spacings from each other.

Figure 5:
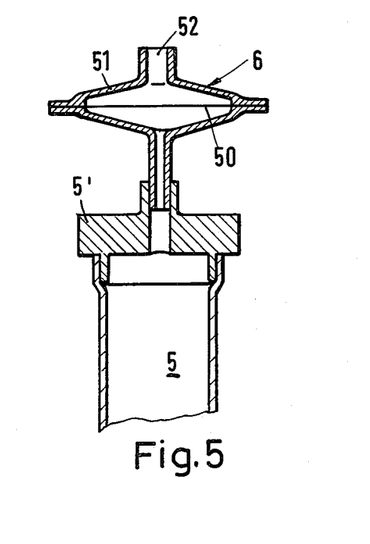
FIG. 5 illustrates one example of a blood pressure equalization device connected to the measuring chamber.

FIG. 5 illustrates one example of a pressure equalization device 6, for example, comprising a membrane 50 held in position in a chamber 51. The membrane is permeable to air but constitutes a barrier to any passage by germs. The outlet port 52 of the chamber 51 will normally connect it to a pressure measuring manometer not shown.

The membrane 50 may also be sufficiently elastic so that air passage is not necessary. In any event, the membrane must prevent the contamination of the blood circulating system. Such membranes are well known in the art. If desired, the membrane may be replaced by a balloon type contamination barrier also well known in the art.

Figure 7:
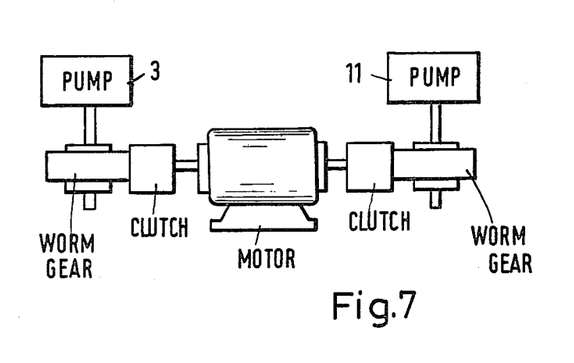
FIG. 7 illustrates an arrangement of the pump drive mechanism in a simplified illustration.

FIG. 7 illustrates the arrangement wherein one motor forming part of the control circuit 13 may drive both pumps 3 and 11, for example, through magnetic clutches and through respective gears, such as worm gears or the like.

Figure 6:
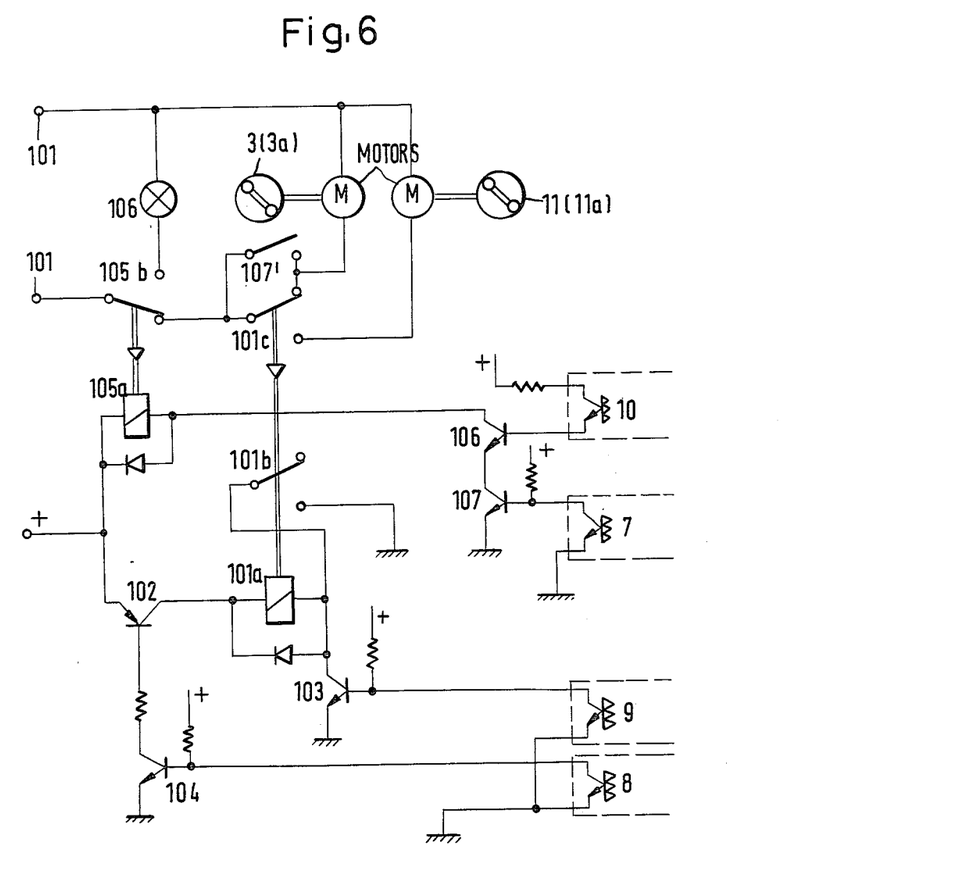
FIG. 6 illustrates the details of the electronic control circuit shown in block form in FIG. 1.

FIG. 6 illustrates one preferred example embodiment of the control circuit 13. A relay 101a switches by means of a double-throw contact 101c between the artery pump 3 or the vein pump 11. The same switching may be employed for operating the valves. Respective motors are energized through the power supply connected to terminals 101. Current for the energization of the relay coil 101a flows through the transistor 102 from the positive pole of a supply voltage source not shown. A further transistor 103 is connected to the other end of the relay 101a and to ground. A normally open holding contact 101b closes and connects the relay coil to ground. The transistors 102 and 103 are controlled by the level sensors 8 and 9. If the filling level in the chamber 5 reaches the upper sensor 9 the light path is interrupted and the photo-transistor does not provide any signal. As a result, the transistor 103 becomes conductive. Simultaneously, the photo-transistor of the sensor 8 is also non-conductive so that the transistor 104 and the transistor 102 become conductive. Under these operating conditions the relay coil 101a receives its energizing current. As a result, the vein blood pump 11 is energized through the double-throw contact 101c. Simultaneously the contact 101b is closed to hold the relay energized even if the blood level should sink within predetermined limits. As soon as the blood level in the chamber 5 drops below the position determined by the sensor 8, the photo-transistor of the sensor 8 becomes conductive, whereby the transistors 104 and 102 become non-conductive and the relay 101a is de-energized. As a result, the double-throw contact 101c energizes the artery blood pump 3 and de-energizes the venous blood pump 11. Thus, one operating cycle is completed and the described operation is repeated.

The circuit arrangement of FIG. 6 further comprises a double-throw contact 105b operated by a relay 105a which closes the motor drive circuit as long as the transistors 106 and 107 responsive to the sensors 7 and 10 receive their energizing current. This is the case as long as the photo-transistor of the sensor 10 receives light and as long as the photo-transistor of the sensor 7 is dark. If the level of the uppermost sensor 10 is exceeded by the blood in the chamber 5, or if the blood level drops below the level determined by the position of the sensor 7, the relay 105 is de-energized thereby also de-energizing the motors. Simultaneously, the contact 105b switches over to provide an alarm signal, for instance, through a light bulb 106.

If the manual switch 107' is closed, the artery pump 3 may then be operated independently of the position of the contact 101c. The r.p.m. of the pump 11 must be larger than the r.p.m. of the pump 3 as will be described in more detail below with reference to the operation of the entire system.

Instead of using two separate motors for driving the pumps and/or valves it is possible to use but one motor in accordance with the illustration of FIG. 7 as described above.

Figure 8:
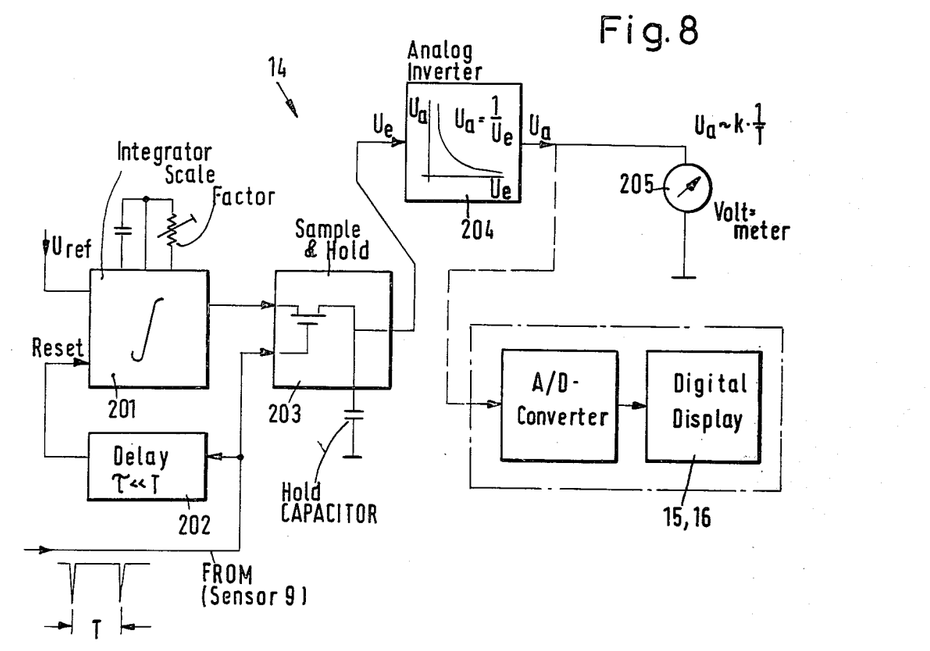
FIG. 8 illustrates an analog computer in block form, suitable for the present invention.

FIG. 8 illustrates an example embodiment of a substantially conventional computer circuit that could be employed to embody the computer 14 shown in FIG. 1. It is the purpose of the computer to realize the function $Q=V/T$, whereby V is the blood volume necessary to fill the measuring chamber 5 between the levels of the inner sensors 8 and 9. This volume is determined by the inner cross sectional diameter of the chamber 5 and the vertical spacing between the sensors 8 and 9 and since these factors are given the respective volume V is a constant. The duration of one cycle is indicated by T. This time is determined by the time necessary for the blood to fall from the level of the sensor 9 to the level of the sensor 8 and to rise again to the level of the sensor 9. The blood flow Q is then determined as the volume per unit of time. For this purpose the duration of a cycle is determined and its reciprocal value is formed. If desired, a multiplying scale factor may be introduced as is well known in the art. The scale factor takes the size of the volume into account and makes sure that the result is displayed in the desired dimension.

The analog computer of FIG. 8 is as such well known in the art.

An example for a digital computer which could also be used in the present context is, for example, disclosed in "IEEE Transactions Actions On Biomedical Engineering", volume BME-20 (1973), pages 468–470.

In FIG. 8 the integrator 201 integrates an input reference voltage $U_{ref}$ provided by a reference voltage source not shown, to produce a saw-tooth voltage at the output of the integrator which is periodically reset by a delay member 202 receiving its input signal from one of the sensors, for example, sensor 9 to determine the cycle duration T. Thus, the peak to which the saw-tooth voltage rises is a measure for the time spacing between the pulses provided by the sensor thus determining the cycle duration T. The sample and hold circuit 203 samples the output of the integrator 201. The sample and hold circuit 203 is also controlled by the input pulses from the sensor. The arrangement is such, due to the delay line 202, that the integrator output is sampled prior to the resetting of the integrator. Thus, at the output of the sample and hold circuit 203, a voltage is provided which is proportional to the duration T of the preceeding work cycle. The output of the sample and hold circuit 203 is connected to an analog inverter 204 which provides at its output its reciprocal 1/T. The analog inverter 204 may comprise, for example, non-linear diode network means or an analog divider with a constant numerator. Such analog dividers are well known in the art, for example, Model 4202 manufactured by Burr Brown, is suitable for the purpose.

The output voltage of the analog inverter may be directly supplied to a indicating meter 205 which would display a mean blood flow rate. Similarly, the output of the inverter 204 may be supplied to an analog-to-digital converter, the output of which is connected to digital display means which are well known in the art.

Figure 9:
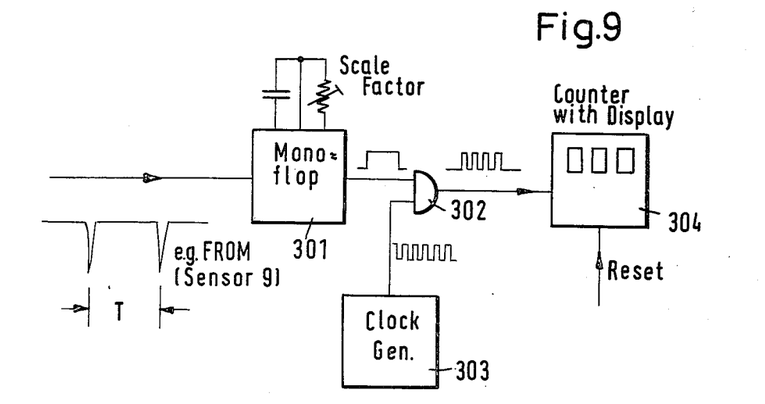
FIG. 9 illustrates a matching or adapting circuit for the display counter.

FIG. 9 illustrates a circuit arrangement for displaying the total blood volume employed, or rather passed through the system during a treatment. The display device 16 shown in FIG. 1 is to indicate such total blood volume and for this purpose it must count the number of work cycles. The blood volume displaced or moved through the chamber 5 between the sensors 8 and 9 is not necessarily an even value, for example, 10 ml. Thus, it is suitable to provide an adaptation between the input signal and the counter and FIG. 9 illustrates such an adaptor. For example, the pulse signals coming from the sensor 9 at periodic intervals are supplied to a mono-flop circuit 301 which converts these pulses into pulses of a predetermined duration as shown at the output of the mono-flop 301. A gate circuit 302 controlled by a clock signal 303 passes a respective number of timing pulses during the duration of the pulse at the output of the circuit 301. The pulses at the output of the gate 302 may then be counted electro-mechanically, or electronically and displayed by well known means. By selecting a suitable ratio of the clock-pulse generator frequency and the time constant of the mono-flop 301, the scale factor may be suitably adjusted as is also well known in the art.

In operation, during the blood withdrawal phase, the blood from the cannula 1 is drawn by the artery pump 3 through the upper leg 2' of the junction member to pump the blood through the blood cleaning device 4 which may, for example, be a dialyzer, an absorption capsule, or a filter, whereupon it is pumped into the measuring chamber 5 made, incidentally, of transparent plastic material and held by the sensors. The connecting port 5''' is preferably connected to the side wall of the chamber 5. However, the invention is not limited to this modification. The connection for the inlet port may also be through any of the caps 5' or 5'', further, the inlet port may be arranged tangentially relative to the housing of the chamber 5 which may be advantageous with regard to achieving a particular flow pattern. The control by means of the above described circuit arrangement is such that the filling level at the beginning of the withdrawal phase during which blood is taken out of the internal circular system of the patient, reaches just slightly above the level determined by the level sensor 8. As now the filling level rises in the chamber 5, the sensor 9 will respond by the fact that light is prevented to pass to the respective light sensitive photo-transistor. The respective signal is then used to terminate the blood withdrawal phase and to start the blood return phase during which blood is pumped through the vein conduit means 11' and to the lower leg 2' of the junction member 2 by the blood pump 11 back into the circulatory system of the patient.

The level sensors 7 and 10 are provided for safety purposes to cause a signal if the filling level in the chamber 5 exceeds or falls below a predetermined variation range which range is determined by the level sensors 8 and 9. The level sensors 7 and 10 cause through the circuit 13, a stopping of the artery pump 3 and/or the vein pump 11 thereby preventing a further undesirable volume shift. Simultaneously, alarm signals may be provided to indicate the nonpermissible operational condition as described above.

The pumps 3 and 11 may, in the simplest embodiment, be driven so that during the withdrawal phase only the artery pump 3 operates with a predetermined r.p.m. whereas the vein pump 11 does not operate at all. In the blood return phase the operation is reversed in that only the vein pump 11 operates with the same or a different pre-selected r.p.m., whereas the pump 3 does not operate.

According to another advantageous embodiment of the invention, the artery pump 3 may operate during the blood withdrawal phase as well as during the blood return phase with a pre-selected r.p.m. or speed, whereas the vein blood pump 11 only operates during the blood return phase with a pumping rate which is larger than the rate of the artery pump. In this manner it is possible to divide the return blood stream pumped by the pump 11, in the junction member 2 so that a proportion is returned to the patient through the cannula 1 and another proportion is pumped again by the artery pump 3 in accordance with the feed or pumping rate of the pump 3, whereby the blood is subjected repeatedly to a cleaning operation, for example.

The ratio of the two partial streams is exactly defined by the pumping rates of the two pumps, whereby the second partial flow is subjected to the cleaning for a second time as mentioned. This feature greatly improves the detoxification efficiency.

The operation may be simplified for the just described type of control of the two pumps by employing but one adjustment device which influences the pumping rates of both pumps in the same manner, whereby the two rates are preferably related to each other by a fixed ratio. Thus, it is possible to drive both pumps with the same motor and the fixed ratio may be determined by the gear means employed as illustrated in FIG. 7. The electronic control circuit may operate the magnetic clutches also shown in FIG. 7, whereby the drive for the vein pump may be de-coupled during the blood withdrawal phase and driven during the blood return phase.

Further modifications of the control device may be provided to gradually control the pumping rate either continuously or in a periodically discontinuous manner between predetermined limit values. In this type of operation it is necessary to make certain that during the withdrawal phase the pumping rate or speed of the artery blood pump 3 is higher than the pumping rate of the vein blood pump 11. Further, it is necessary to make sure that during the blood return phase the pumping speed of the vein blood pump is higher than the pumping speed or rate of the artery pump 3.

The pumping rates may also be influenced by valves 3a and 11a, for example, electromagnetically operated hose clamping valves which are located upstream of their respective pump. Such valves are especially useful where the blood pumps are provided in the form of self controlling hose pumps having a relatively flexible pump hose. Such hose pumps which are known as such are advantageous because they produce only a limited reduced pressure at their input port since the pump hose flattens out in response to a small reduced pressure, thereby reducing the pump rate substantially. In the extreme situation the pump rate may become zero. Such reduced pressure limitation of the pump rate is especially suitable for the artery pump 3 because it prevents the undesirable situation that the cannula 1 inserted into the blood vessel of the patient attaches itself by suction to the inner surface of the blood vessel wall as could happen if there is a too large reduced pressure between the inner wall surface of the blood vessel and the free end of the cannula 1.

Where hose pumps are used having a relatively rigid pump hose, it is necessary to specially monitor the pressure at the inlet port of the artery pump so that said pressure remains within predetermined limits. For this purpose a well known manometer including limit contacts may be employed.

Similarly, hose pumps of this type may cause a pressure limitation at their output port because a backflow inside the pump hose may occur above a certain value of the output pressure, whereby the effective pumping rate is respectively diminished.

The particular characteristics of the apparatus according to the invention are especially compatible with the above mentioned self controlling features of hose pumps because a disadvantage of these pumps which occurs when these pumps are used in different environments, is compensated according to the invention. Such disadvantage is seen in that a precise control of the blood flow is made more difficult due to the above mentioned dependency of the pump rate from the input pressure and from the output pressure. However, the invention makes good use thereof.

Contrary to prior art devices, the apparatus according to the invention, permits by relatively simple and inexpensive means, a continuous measuring and monitoring of the quantity of blood which flows per unit of time through the external blood circulatory system. In this context the invention makes good use of the fact that the periodic change or variation of the filling level in the measuring chamber 5 between the response level of the sensors 8 and 9 corresponds respectively to a predetermined volume that has been pumped or moved through the chamber. These volumes may be divided by the duration of a cycle, whereby the mean blood value is obtained as described above. In order to indicate the mean blood flow value, the computer circuit 14 is provided and performs the computation for each operational cycle by electronic means to provide an input signal to the display device 15 showing the mean blood flow value as described above. A further indicator 16 is a counter and indicates the total quantity of blood that has passed through the external circulatory system.

As described, the control circuit 13 or the computer 14 may comprise a monitoring circuit to make sure that the blood flow does not exceed a certain predetermined upper level and does not fall below a pre-selected minimum value. Further, the monitoring circuit makes sure that a stoppage in the blood flow is automatically recognized to provide an alarm signal signifying such a situation. Thus, the alarm signal may, for example, be provided when the duration of a certain work cycle exceeds a predetermined maximum value. This type of arrangement eliminates troubles in the operation since they are recognized at an early stage of their occurrence. Such troubles may, for instance, be caused by flow impeding situations such as blood clots or by larger leaks in the conduit system. The invention does eliminate these problems.

Incidentally, the above described level sensors 7, 8, 9, and 10 are all of the photo-electric type. However, it will be appreciated that other sensors such as capacitive sensors, or sound or ultra-sound sensors may also be used. Further, a float may be provided in the measuring chamber 5 which is specifically lighter than blood and the position of which could be detected, for example, by magnetically sensitive sensors.

Although the invention has been described with reference to specific example embodiments, it will be appreciated, that it is intended to cover all modifications and equivalents within the scope of the appended claims.

What is claimed is:

1. A blood flow monitoring and control apparatus, comprising single needle liquid withdrawal and liquid return means (1) connectable to a patient, blood treating means (4), first artery conduit means (3') connecting said blood treating means to said single needle means, artery pump means (3) in said first artery conduit means, a single operating condition volume sensing means (5) having an inlet and an outlet, second artery conduit means operatively interconnecting said blood treating means (4) to said inlet of said single operating condition volume sensing means (5), vein conduit means (11') and vein pump means (11) in said vein conduit means operatively connecting said outlet of said single operating condition volume sensing means (5) to said single needle means to form together with said first conduit means a closed loop flow circuit in which the blood circulates in but one direction, and control means (13) operatively connected to said single operating condition volume sensing means (5) as well as to said artery and vein pump means (3, 11) to control the blood flow in said closed loop flow circuit, said operating condition volume sensing means comprising filling level sensing means 7, 8, 9, 10 for the volumetric measuring of the liquid flowing in said one direction in said closed loop flow circuit, said filling level sensing means providing control signals for a liquid withdrawal phase from said volume sensing means (5) through said vein conduit and vein pump means (11, 11') and for a liquid return phase to said volume sensing means (5) through said artery conduit and artery pump means (3, 3'), whereby the liquid withdrawal phase is stopped upon reaching a predetermined first filling level in said volume sensing means (5) and the liquid return phase is started whereas a liquid return phase is stopped upon reaching a predetermined second filling level and vice versa.

2. The apparatus of claim 1, further comprising pressure equalization means operatively connected to said volume level sensing means.

3. The apparatus of claim 1, wherein said filling level sensing means comprise a plurality of individual sensors and means for adjusting the elevational position of said sensors.

4. The apparatus of claim 1, wherein said filling level sensing means comprise measuring chamber means and a plurality of individual sensors, a first pair of said sensors being arranged for sensing the upper and lower limit of a normal filling level condition in said measuring chamber for limiting the normal filling level condition to be within said upper and lower limit, a second pair of said sensors being arranged to detect the exceeding of said upper limit and the dropping below said lower limit respectively of the filling level condition in said measuring chamber, said first pair of sensors (8, 9) being operatively connected to said control means for controlling said pump means so as to maintain the normal filling level condition in said measuring chamber means, said second pair of sensors (7, 10) being connected to said control means for stopping said pump means.

5. The apparatus of claim 4, further comprising means operatively connected to said control means for indicating the filling condition in said measuring chamber means.

6. The apparatus of claim 5, wherein said indicating means indicate an unpermissible operating condition.

7. The apparatus of claim 1, further comprising valve means in said first and second conduit means, and means operatively connecting said valve means to said control means.

8. The apparatus of claim 7, wherein said single needle liquid withdrawal and liquid return means comprise an inlet port proper, a conduit connected for liquid withdrawal and a conduit connected for liquid return, both conduits being connected to said inlet port proper, said control means being arranged to control said pump means and said valve means so that the flow rate is higher in said liquid withdrawal conduit during a liquid withdrawal phase while it is lower in said liquid return conduit and vice versa during the liquid return phase.

9. The apparatus of claim 1, wherein said control means further comprise electronic computer means operatively connected to said control means, and indicating means operatively connected to said computer means which calculate a blood flow mean value for each operational cycle, said indicating means displaying said blood flow mean value.

10. The apparatus of claim 9, wherein said control means further comprise monitoring circuit means which recognize the deviations from a preselected blood flow mean value to provide a warning.

11. The apparatus of claim 10, wherein said monitoring circuit means also recognize the stopping of the blood flow to provide a warning.

12. The apparatus of claim 1, wherein said control means further comprise flow quantity measuring means including counter means for indicating the total volume of blood flowing through the apparatus.

* * * * *